United States Patent [19]

Chin et al.

[11] Patent Number: 4,713,232

[45] Date of Patent: Dec. 15, 1987

[54] PROCESS FOR THE DESTRUCTION OF BY-PRODUCT TETRANITROMETHANE

[75] Inventors: Chang-Hwa Chin, Brossard; Anthony C. F. Edmonds, North York; Colin M. Evans, Toronto, all of Canada

[73] Assignee: C-I-L Inc., North York, Canada

[21] Appl. No.: 896,094

[22] Filed: Aug. 13, 1986

[30] Foreign Application Priority Data

Apr. 9, 1986 [CA] Canada .................................. 506238

[51] Int. Cl.[4] .................... C01B 21/46; C01B 21/38
[52] U.S. Cl. ................................. 423/390; 423/236; 568/944; 568/948; 149/124
[58] Field of Search ............... 568/926, 935, 944, 948; 423/236, 390, 390 P; 149/124

[56] References Cited

U.S. PATENT DOCUMENTS

| | | | |
|---|---|---|---|
| 1,632,959 | 6/1927 | Gärtner | 568/944 X |
| 3,781,374 | 12/1973 | Fossan | 568/944 |
| 4,001,373 | 1/1977 | Hall et al. | 568/926 X |
| 4,003,977 | 1/1977 | Gilligan et al. | 568/926 X |

OTHER PUBLICATIONS

Urbanski, T., *Chemistry and Technology of Explosives,* vol. I, MacMillan Co., N.Y., 1964, pp. 588–594.

*Primary Examiner*—Edward A. Miller
*Assistant Examiner*—Susan Wolffe
*Attorney, Agent, or Firm*—Donald G. Ballantyne

[57] ABSTRACT

A process for the management of by-product tetranitromethane (TNM) which avoids the hazards of the prior art isolation or extraction procedures. A selected in-plant liquid or vapor stream, or a reactor off-gas stream from nitration or nitric acid oxidation plant, which contains TNM, is heated to effectively pyrolyze the TNM without undue losses of nitric acid values.

7 Claims, No Drawings

PROCESS FOR THE DESTRUCTION OF BY-PRODUCT TETRANITROMETHANE

This invention relates to processes where organic materials are treated with nitric acid. In particular, the invention provides a separate secondary process for the early interception and economical continuous destruction of a dangerous by-product of nitric acid based oxidation or nitration reactions.

The said nitration and oxidation reactions are well known and widely practised in industry. They provide valuable products, such as, explosives and intermediates for the manufacture of pharmaceuticals, dyestuffs, plastics, pesticides and many other materials of commerce. Less well known is that many of these processes also produce amounts of a dangerous by-product, tetranitromethane (TNM).

TNM is dangerous for two reasons. Firstly, because of its high toxicity. It is rapidly absorbed by skin contact or on inhalation of the vapour. Secondly, though TNM is not an explosive in the pure state, it readily dissolves hydrocarbons and other non-polar fuels producing water immiscible, dense, explosive liquids which can show great explosive power and high sensitivity.

The amount of TNM made as a by-product of other processes is usually quite small. However, modern practices of recovery and reconcentration of nitrogenous fumes and of residual nitric acid present in spent acid, can lead to the TNM recycling to reactors in recovered nitric acid. A gradual, cumulative, build-up in TNM concentration which presents an increased level of potential hazard is, therefore, possible even when only minor amounts are produced.

The presence of TNM contamination in products is known to present hazards. In the case of trinitrotoluene, toxic effects have been noted on magazine workers. With some nitroglycerine-based explosives, reductions in safe shelf storage times have been recorded. In order to avoid these problems, products have been washed with mildly alkaline sulphite solutions. TNM is abstracted by this treatment, into the wash liquid as a toxic sulphite salt of trinitromethane. However, such a treatment is not possible with water soluble products.

TNM is a volatile material. Quantities frequently escape from reactors where it is formed as vapour in the reactor off-gases. These gases contain, in addition, nitrogen oxides and, usually, nitric acid vapour. Recovery processes designed to separate these gaseous materials, and to prevent environmental pollution, consist of scrubbing the air diluted gases with dilute nitric acid. TNM is unaffected by this treatment and passes through the system to be discharged with stack gases. This presents a possible pollution hazard and represents a waste of the recoverable nitrogen content in the TNM. There is also a possibility that the TNM may be condensed as a separate liquid phase in cool conditions in absorbers with obvious potential hazard. Processes have been developed to minimize these discharges and to abstract the TNM from any such stack gas streams as a saleable derivative. U.S. Pat. Nos. 4,001,373 and 4,003,977 describe the absorption of the TNM as trinitromethide salts by aqueous alkaline scrubbing of the gas stream. Subsequent acidification of the spent scrubber fluid releases trinitromethane. This is a potentially dangerous substance with very similar properties to TNM. A disadvantage of the above processes consists of high use of alkali whenever appreciable amounts of carbon dioxide are present in the treated gas stream. It appears that these factors, together with the size and complexity of the equipment needed, have prevented wide application of the processes.

Where chemical reactors are operated at moderate or low temperatures, by-product TNM may remain in solution in spent acids. Recovery operations tend to concentrate the volatile, oleophilic TNM in highly concentrated nitric acid and to recycle the material. U.S. Pat. No. 3,781,374 describes a means of separating TNM from such a nitric acid source. Careful distillation of the nitric acid gives a most volatile cut approaching an azeotropic concentration of 30% TNM in over 99% nitric acid. Separation of this fraction followed by water dilution and cooling can give a separate layer of TNM under dilute nitric acid. Running-off the TNM and a subsequent water wash provides TNM of saleable quality. The dilute nitric acid stream which is simultaneously produced, may be reconcentrated and recycled at considerable cost. The economics of this process, the low demand for TNM and the dangers in handling the pure material appear to have militated against the wide application of this invention.

There exists, therefore, a need for a simple process capable of avoiding completely the toxicity and explosive risks associated with TNM made as a by-product.

Accordingly, it is an object of this invention to provide a safe economic means for the destruction of the TNM by-product of nitric acid based processes, which means avoids the hazards and deficiencies associated with known procedures.

Another object is to provide for the destruction of TNM without loss of valuable recoverable nitrogen fractions. These nitrogen fractions include nitrogen oxides naturally formed by the destruction of the TNM. A minimal amount of additional nitrogen oxides is formed by the simultaneous decomposition of nitric acid.

Specifically, the process of the present invention provides for the selective destruction of TNM in the presence of other gases including nitric acid vapour, and comprises heating the mixture containing TNM to temperatures ranging from 215° to 300° C., preferably from 220° to 300° C. and, most preferably, from 220° to 250° C., and maintaining the temperature for from 0.1 to 100 seconds, preferably from 0.5 to 5 seconds. Subsequently, the product mixture may be cooled and otherwise processed to recover the valuable nitrogen fractions present.

The decomposition of TNM at elevated temperatures has been known for some time. However, it has been surprisingly found that the naturally unstable nitric acid, necessarily present whenever early, economic interception of the TNM is practised, largely survives the severe heat treatment which destroys the TNM. The economic success of this invention is largely dependent on this surprising observation. This is because, though it is technically feasible to reconstitute concentrated nitric acid from nitrogen oxides, it is expensive. The reasons for this expense is that the process involves the use of large equipment for absorption as dilute nitric acid followed by use of considerable amounts of energy in the reconcentration processes.

In order that the invention may be better understood, preferred embodiments will now be described by way of the following examples.

EXAMPLE 1

A proprietary process for the nitration of an aromatic compound to produce a plastics intermediate uses nitric acid as the nitration medium. The product mixture issuing from the nitration reactors is a solution of the plastics intermediate in nitric acid which is then fed to a falling film evaporator. In the evaporator, most of the nitric acid and the TNM are removed overhead as vapour. Two-stage condensation of the vapour gives, as more volatile condensate, 2250 kg/hr of over 99% nitric acid containing 13.5 kg/hr of TNM (together with dissolved NOX). After treatment in a bleacher, which strips out most of the dissolved NOX, the stripped condensate stream is fed to a continuous distillation column. A most volatile top fraction of 44 kg/hr of over 99% nitric acid containing 12 kg/hr of TNM is removed as gas along with some residual NOX and oxygen. This gas and vapour stream is fed, without condensation, to a pyrolyser unit consisting of a tantalum tube. The tube is heated by external electrical elements so the gas mixture passing therethrough reaches 250° C. and the tube is sized so the residence time of the gas is one second. In this unit, 99% of the TNM is converted to carbon oxides and NOX and less than 40% of the nitric acid is decomposed. All of this mixture of gaseous products is fed, in admixture with dilution air, to a waste gas scrubber tower where the nitric acid and NOX, (from this and other locations in the nitration plant) is absorbed in dilute nitric acid. The fortified dilute nitric acid from this tower is recovered by reconcentration, while the carbon oxides, produced by decomposition of the TNM, are discharged to the atmosphere.

EXAMPLE II

A system for the nitration of a chemically resistant chlorinated aromatic substrate, which produces a herbicide intermediate, uses a mixture of concentrated nitric and sulphuric acids at 100° to 115° C. in a series of reactors. Off-gases from this reactor series consist of 60 kg/hr of a mixture of chlorine and hydrogen chloride, 11 weight percent; carbon dioxide, 55%; carbon monoxide, 1%; nitric acid vapour, 25%; water, 1% and TNM 4.5%. Passage of this gas mixture to a pyrolyser unit consisting of an electrically heated quartz tube raises the temperature of the gas mixture to 250° C. for one second. This exposure destroys over 99% of TNM while leaving 99% of the nitric acid undecomposed. Passage of this gas stream to a cooler, and then to a gas scrubber using sulphuric acid as absorbing liquid, removes effectively all the nitric acid and NOX leaving chlorine, hydrogen chloride and carbon dioxide for subsequent treatment in a selective absorption unit before discharge to the atmosphere. The nitric acid and NOX solution in the sulphuric acid is subsequently used to produce new nitrating acid mixture.

While it will be obvious to those skilled in the art that pyrolysis or thermal decomposition of the TNM may be practised at several junctures, it is most advantageous to practise the invention at a location where the TNM is highly concentrated so that heating and cooling requirements are minimized. It is also advantageous to minimize the amounts of nitric acid simultaneously subjected to the pyrolysis conditions so as to minimize both losses through decomposition of the acid and reconstitution costs. It is usually also advantageous to arrange that the pyrolysis takes place before feeding of the vapour or gas stream to an absorption unit.

We claim:

1. A process for the destruction of tetranitromethane which is present in admixture with nitric acid as a by-product of the nitric acid treatment of an organic substance, which destruction process comprises subjecting the tetranitromethane and nitric acid mixture to a temperature of at least 210° C. whereby the tetranitromethane fraction is decomposed and the nitric acid fraction is substantially preserved for recovery.

2. A process as claimed in claim 1 wherein the said tetranitromethane and nitric acid mixture is heated to a temperature of from 210° to 300° C. for a period of from 0.1 to 200 seconds.

3. A process as claimed in claim 1 wherein the nitric acid treatment process is a nitration process.

4. A process as claimed in claimed 1 wherein the nitric acid treatment process is an oxidation process.

5. A process as claimed in claim 1 wherein the said tetranitromethane and nitric acid mixture comprises off-gases and vapours.

6. A process as claimed in claim 5 wherein the said off-gases and vapours are heated to a temperature of from 220° to 250° C. for a period of from 0.5 to 100 seconds.

7. A process as claimed in claim 1 wherein the said tetranitromethane and nitric acid mixture is heated to a temperature of from 220° to 250° C. for from 0.5 to 100 seconds.

* * * * *